(12) United States Patent
Sherwood

(10) Patent No.: US 7,963,999 B2
(45) Date of Patent: Jun. 21, 2011

(54) METHOD FOR CONNECTING ELECTRODES HAVING APERTURES

(75) Inventor: Gregory J. Sherwood, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 4 days.

(21) Appl. No.: 12/287,858

(22) Filed: Oct. 14, 2008

(65) Prior Publication Data

US 2009/0044404 A1 Feb. 19, 2009

Related U.S. Application Data

(60) Division of application No. 11/383,074, filed on May 12, 2006, now Pat. No. 7,443,652, which is a continuation of application No. 11/112,656, filed on Apr. 22, 2005, now Pat. No. 7,092,241.

(51) Int. Cl.
*H01G 9/00* (2006.01)
*H01M 2/12* (2006.01)

(52) U.S. Cl. ............... 29/25.03; 29/25.41; 29/25.42; 361/521; 361/509; 607/5

(58) Field of Classification Search ............ 29/825, 29/830, 846–852, 25.01–25.03, 25.35–25.42; 361/508–518, 523, 528; 438/253, 386, 393, 438/398; 607/36, 5, 607; 257/209, 532, 257/910
See application file for complete search history.

(56) References Cited

U.S. PATENT DOCUMENTS

| | | | |
|---|---|---|---|
| 2,021,455 A | 11/1935 | Lilienfeld | |
| 3,398,333 A | 8/1968 | Zeppieri | |
| 4,232,099 A | 11/1980 | Sullivan | |
| 4,614,194 A | 9/1986 | Jones et al. | |
| 4,616,655 A | 10/1986 | Weinberg et al. | |
| 4,659,636 A | 4/1987 | Suzuki et al. | |
| 4,907,130 A | 3/1990 | Boulloy et al. | |
| 5,550,706 A | 8/1996 | Kurzweil et al. | |
| 5,801,917 A | 9/1998 | Elias | |
| 5,855,995 A | 1/1999 | Haq et al. | |
| 5,926,357 A | 7/1999 | Elias et al. | |
| 5,949,638 A | 9/1999 | Greenwood, Jr. et al. | |
| 6,006,133 A | 12/1999 | Lessar et al. | |
| 6,110,233 A | 8/2000 | O'Phelan et al. | |
| 6,242,128 B1 | 6/2001 | Tura et al. | |
| 6,275,729 B1 | 8/2001 | O'Phelan et al. | |
| 6,309,532 B1 * | 10/2001 | Tran et al. | 205/687 |
| 6,413,283 B1 | 7/2002 | Day et al. | |
| 6,421,226 B1 | 7/2002 | O'Phelan et al. | |
| 6,470,545 B1 * | 10/2002 | Branchevsky | 29/25.42 |

(Continued)

OTHER PUBLICATIONS

"U.S. Appl. No. 11/112,656, Amendment and Response filed Dec. 12, 2005 to Non-Final Office Action Aug. 11, 2005", 10 pgs.

(Continued)

*Primary Examiner* — Minh Trinh
(74) *Attorney, Agent, or Firm* — Schwegman, Lundberg & Woessner, P.A.

(57) ABSTRACT

One embodiment includes a method that includes positioning a first substantially planar electrode including material defining a first aperture into a capacitor stack in alignment with a second substantially planar electrode such that a first non-aperture portion of the second substantially planar electrode at least partially overlays the first aperture and joining the first substantially planar electrode to the second substantially planar electrode proximal the material defining the first aperture and the first non-aperture portion of the second substantially planar electrode.

20 Claims, 6 Drawing Sheets

U.S. PATENT DOCUMENTS

| | | | |
|---|---|---|---|
| 6,493,212 B1 * | 12/2002 | Clarke et al. | 361/521 |
| 6,509,588 B1 | 1/2003 | O'Phelan et al. | |
| 6,522,525 B1 | 2/2003 | O'Phelan et al. | |
| 6,556,863 B1 | 4/2003 | O'Phelan et al. | |
| 6,571,126 B1 | 5/2003 | O'Phelan et al. | |
| 6,621,686 B1 | 9/2003 | Jenn-Feng et al. | |
| 6,648,928 B2 | 11/2003 | Nielsen et al. | |
| 6,687,118 B1 | 2/2004 | O'Phelan et al. | |
| 6,699,265 B1 | 3/2004 | O'Phelan et al. | |
| 6,861,670 B1 | 3/2005 | Ohtani et al. | |
| 6,885,548 B2 | 4/2005 | Nyberg | |
| 6,922,330 B2 | 7/2005 | Nielsen et al. | |
| 7,092,241 B2 | 8/2006 | Sherwood | |
| 7,224,575 B2 | 5/2007 | Sherwood | |
| 7,443,652 B2 * | 10/2008 | Sherwood | 361/508 |
| 2003/0056350 A1 | 3/2003 | Yan et al. | |
| 2003/0199940 A1 | 10/2003 | Nyberg | |
| 2004/0085712 A1 | 5/2004 | Tadanobu et al. | |
| 2004/0147961 A1 | 7/2004 | O'Phelan et al. | |
| 2004/0220627 A1 | 11/2004 | Crespi et al. | |
| 2006/0012943 A1 | 1/2006 | Sherwood | |
| 2006/0166088 A1 | 7/2006 | Hokanson et al. | |
| 2006/0238959 A1 | 10/2006 | Sherwood | |
| 2007/0162077 A1 | 7/2007 | Sherwood | |

OTHER PUBLICATIONS

"U.S. Appl. No. 11/112,656, Non-Final Office Action mailed Aug. 11, 2005", 12 pgs.

"U.S. Appl. No. 11/112,656, Notice of Allowance mailed Jan. 12, 2006", 6 pgs.

"U.S. Appl. No. 11/112,656, Supplemental Notice of Allowance May 1, 2006", 2 pgs.

"U.S. Appl. No. 11/383,074, Notice of Allowance mailed Jun. 19, 2008", 4 pgs.

"U.S. Appl. No. 11/383,074, Response filed Nov. 8, 2007 to Restriction Requirement mailed Oct. 9, 2007", 9 pgs.

"U.S. Appl. No. 11/383,074, Response filed Apr. 14, 2008 to Non-Final Office Action mailed Jan. 14, 2008", 9 pgs.

"U.S. Appl. No. 11/383,074, Restriction Requirement mailed Oct. 9, 2007", 5 pgs.

"U.S. Appl. No. 11/383,074, Non-Final Office Action mailed Jan. 14, 2008", 10 pgs.

Sherwood, G. J., "Method and Apparatus for Providing Flexible Partially Etched Capacitor Electrode Interconnect", U.S. Appl. No. 60/588,905, filed Jul. 16, 2004, 241 pgs.

* cited by examiner

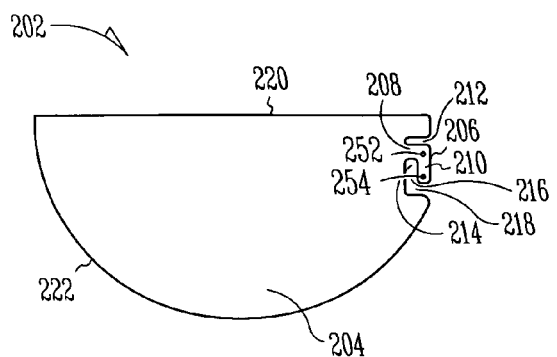
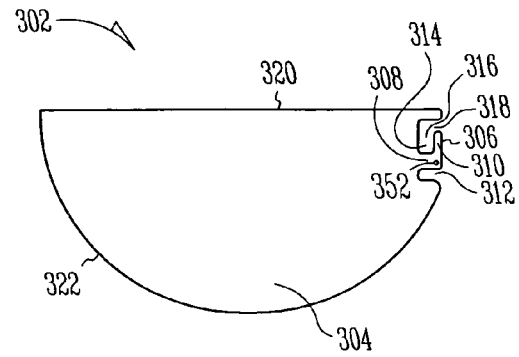
FIG. 2A            FIG. 2B
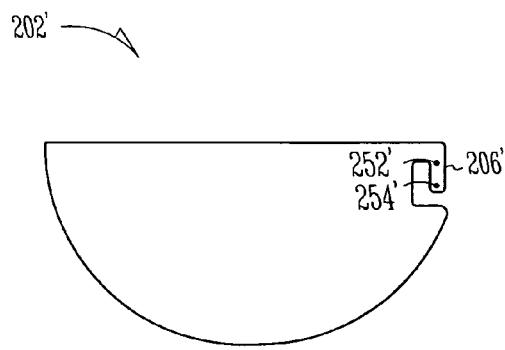
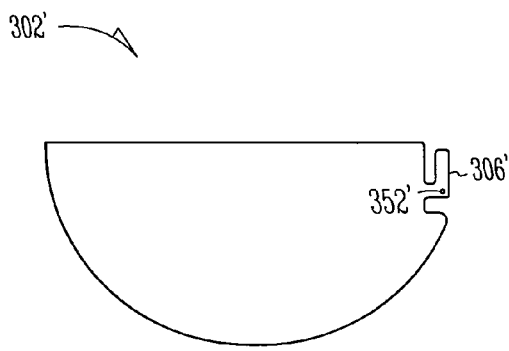
FIG. 3A            FIG. 3B

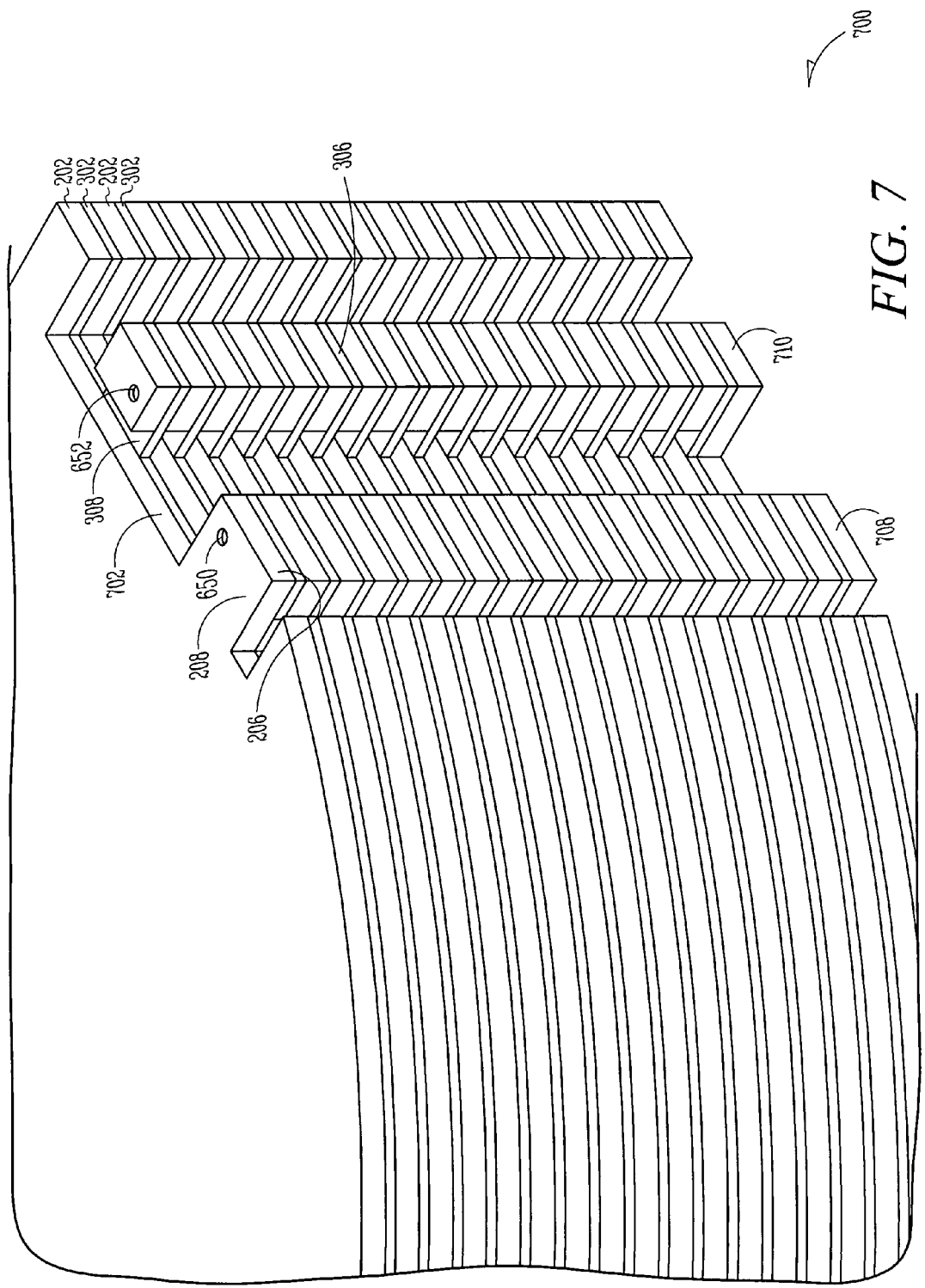

METHOD FOR CONNECTING ELECTRODES HAVING APERTURES

CROSS REFERENCE TO RELATED APPLICATIONS

The present application is a divisional of U.S. patent application Ser. No. 11/383,074, filed May 12, 2006, issued as U.S. Pat. No. 7,443,652, which is a continuation of U.S. patent application Ser. No. 11/112,656, filed on Apr. 22, 2005, issued as U.S. Pat. No. 7,092,241, and the specification of each is incorporated herein by reference in its entirety.

The following commonly assigned U.S. patents are related to the present application and are incorporated herein by reference in their entirety: "High-Energy Capacitors for Implantable Defibrillators," U.S. Pat. No. 6,556,863, filed Oct. 2, 1998, issued Apr. 29, 2003; "Flat Capacitor Having Staked Foils and Edge-Connected Connection Members," U.S. Pat. No. 6,687,118, filed Nov. 3, 2000, issued Feb. 3, 2004; "Flat Capacitor for an Implantable Medical Device," U.S. Pat. No. 6,699,265, filed Nov. 3, 2000, issued Mar. 2, 2004. Additionally, the following commonly assigned Provisional U.S. Patent Application is related to the present application and is incorporated herein by reference in its entirety: "Method and Apparatus for Single High Voltage Aluminum Capacitor Design," Ser. No. 60/588,905, filed on Jul. 16, 2004.

TECHNICAL FIELD

This disclosure relates generally to energy storage devices, and more particularly, to method and apparatus for connecting electrodes having apertures.

BACKGROUND

There is an ever-increasing interest in making electronic devices physically smaller. Consequently, electrical components become more compact as technologies are improved. However, such advances in technology also bring about additional problems. One such problem involves interconnects between various components and interconnects within components.

Interconnects are especially problematic with devices incorporating multiple layers. One such component is the capacitor. Capacitors provide improved charge storage and energy density using multiple conductive layers and advanced dielectrics. As the layers become more complex and smaller in dimensions, problems arise with interconnections.

Thus, there is a need in the art for improved technologies for interconnects between layered devices. The systems used to interconnect the multiple layers should be readily adapted for manufacturing. The interconnects should form robust connections without damaging the multiple layers and without sacrificing substantial performance of the component.

SUMMARY

The above-mentioned problems and others not expressly discussed herein are addressed by the present subject matter and will be understood by reading and studying this specification.

One embodiment of the present subject matter includes positioning a first substantially planar electrode including material defining a first aperture into a capacitor stack in alignment with a second substantially planar electrode such that a first non-aperture portion of the second substantially planar electrode at least partially overlays the first aperture and joining the first substantially planar electrode to the second substantially planar electrode proximal the material defining the first aperture and the first non-aperture portion of the second substantially planar electrode.

One embodiment of the present subject matter includes a capacitor stack including a plurality of substantially planar electrode layers and connection means for laser welding a first substantially planar electrode of the plurality substantially planar electrode layers to a second substantially planar electrode of the plurality substantially planar electrode layers, the weld located toward the center of the capacitor stack.

One embodiment of the present subject matter includes a capacitor stack including a plurality of substantially planar electrodes, a first substantially planar anode disposed in the capacitor stack, the first substantially planar anode including a first etched portion, a first unetched portion, and material defining a first aperture extending through the first unetched portion, a second substantially planar anode having a second etched portion and a second unetched portion, a capacitor case including a first opening sized for passage of the capacitor stack, with the capacitor stack disposed in the capacitor case, a substantially planar cathode disposed in the capacitor stack and connected to the capacitor case, electrolyte disposed in the capacitor case, a first seal connecting a conforming cover to the first opening, the first seal adapted to resist the flow of electrolyte, an anode terminal connected to the first and second substantially planar anode and passing through the case, with a second seal sealing the anode terminal to the capacitor case, the second seal adapted to resist the flow of electrolyte, a cathode terminal connected to the capacitor case, cardiac rhythm management electronics connected to the anode terminal and the cathode terminal and a hermetically sealed device housing the capacitor case and the cardiac rhythm management electronics, wherein the first and second substantially planar anodes are in alignment with a first laser weld connecting the material defining the first aperture and the second unetched portion.

Options within the scope of the present subject matter connect electrodes with laser welding, with molten metal spray, and with connection members. Some embodiments optionally cut connection members to isolate anodes from cathodes. Optional configurations include additional layers with additional apertures overlaying other layers. Some embodiments optionally include portions which are not etched. Capacitors within the present scope are optionally disposed in an implantable medical device.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

FIG. 2A is a top view of an anode for use in constructing a capacitor according to one embodiment of the present subject matter.

FIG. 2B is a top view of a cathode for use in constructing a capacitor according to one embodiment of the present subject matter.

FIG. 3A is a top view of an anode for use in constructing a capacitor according to one embodiment of the present subject matter.

FIG. 3B is a top view of a cathode for use in constructing a capacitor according to one embodiment of the present subject matter.

FIG. 7 is a partial perspective view of cut capacitor stack connection members, according to one embodiment of the present subject matter.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Power sources with stacked planar or substantially planar electrodes are used to power electronic devices. For example, flat electrolytic capacitors having stacked foils are used in implantable medical devices such as implantable cardioverter defibrillators. Capacitors include anodes and cathodes, and in various embodiments, the anodes and cathodes are divided into interconnected foil shaped subcomponents.

The anodes, cathodes, and separator subcomponents are stacked in alignment, in various embodiments. Some embodiments include layered subcomponents with connection members used for interconnecting multiple layers. In some of these embodiments, a connection member protrudes from the main body of the capacitor stack for interconnection to other connection members and/or to terminals and other components. For example, a number of anode connection members extend away from a capacitor stack for interconnection of multiple capacitor anode subcomponent layers. Connection members are additionally used for cathode subcomponents, in some embodiments.

Some capacitor layers of the present subject matter are organized into elements. Elements simplify manufacturing, in various embodiments. Various examples of an element include at least one anode layer and at least one cathode layer. A number of elements may be interconnected to form a capacitor stack. Elements are used during capacitor construction to customize capacitor parameters, such as size, shape, power, and voltage, in various embodiments. For example, elements of a standard size, having a selected thickness, can be used to create multiple capacitors of varying thicknesses.

Figure 1:
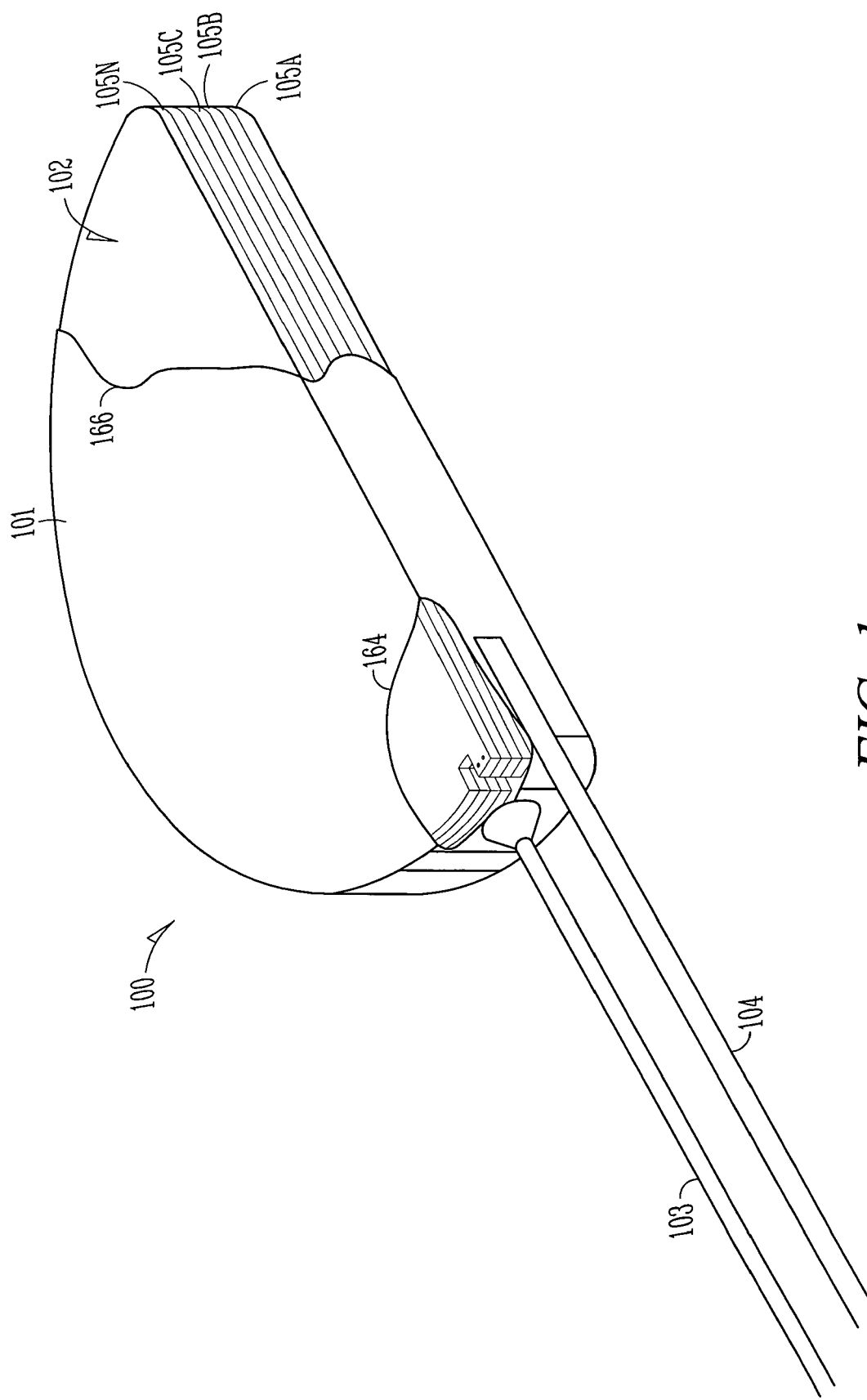
FIG. 1 is a perspective view of a flat capacitor according to one embodiment of the present subject matter.

FIG. 1 shows a flat capacitor 100 constructed according to one embodiment of the present subject matter. Although capacitor 100 is a D-shaped capacitor, in various embodiments, the capacitor is another shape, including, but not limited to, rectangular, circular, oval or other symmetrical or asymmetrical shapes. In various embodiments, capacitor 100 includes a case 101 which contains a capacitor stack 102. In one embodiment, case 101 is manufactured from a conductive material, such as aluminum or titanium. In various embodiments, the case is manufactured using a nonconductive material, such as ceramic or plastic.

Capacitor 100 includes a first terminal 103 and a second terminal 104 for connecting capacitor stack 102 to an outside electrical component. In some embodiments, the capacitor is connected to cardiac rhythm management circuitry, including defibrillator, cardioverter, and pacemaker circuitry. In some embodiments, terminal 103 is a feedthrough assembly insulated from case 101. In some embodiments, terminal 104 is directly connected to case 101. In various embodiments, the capacitor incorporates additional connection structures and methods. The present subject matter incorporates by reference, but is not limited to, additional connection structures and methods illustrated on or around pages 12-13, 59-60, 63-82 of related and commonly assigned Provisional U.S. Patent Application "Method and Apparatus for Single High Voltage Aluminum Capacitor Design," Ser. No. 60/588,905, filed on Jul. 16, 2004, incorporated herein by reference.

Capacitor stack 102 includes at least one cathode, at least one separator, and at least one anode. The capacitor is electrolytic, in various embodiments. Some capacitor components are illustrated through break lines 164, 166 for explanation. In various embodiments, the components occupy a stack of layered subcomponents. In some embodiments, these components are organized into capacitor elements 105A, 105B, 105C, . . . , 105N, illustrated through break line 166. In various embodiments, capacitor stack 102 is formed in two steps, including a first step of stacking capacitor components into two or more elements 105A, 105B, 105C, . . . , 105N, and a second step of stacking elements into a capacitor stack 102. Additional embodiments include forming a capacitor stack in a single step, or three or more steps.

In various embodiments, the cathode includes at least one substantially planar electrode. Various cathode embodiments are metallic. Some cathode examples include a plurality of substantially planar layer subcomponents which are interconnected. Some of these interconnected groups are organized into elements.

In various embodiments, the cathode is coupled to conductive case 101. In some of these embodiments, terminal 104 is attached to conductive case 101, providing a connection between the cathode and outside components such as circuitry. In some embodiments, the cathode is coupled to a feedthrough conductor extending through one or more feedthrough assemblies.

In various embodiments, a separator is used for insulating anodic subcomponents from cathodic subcomponents. Insulation can be provided with an air gap. However, in additional embodiments, one or more sheets of insulative material, such as kraft paper, isolate the anode from the cathode. In some of these embodiments, separator papers provide various functions, such as wicking electrolyte for deposition around the anode and the cathode. Separators can also assist in shaping electrical fields to reduce instances of breakdown.

In various embodiments, capacitor stack 102 includes at least one substantially planar anode. Varying examples include a plurality of substantially planar layer subcomponents interconnected using a variety of methods and structures, including welding. Some embodiments are organized into elements. In various embodiments, an anode includes aluminum, tantalum, hafnium, niobium, titanium, zirconium, and combinations of these metals. In one embodiment, at least portions of a major surface of each anode is roughened and/or etched to increase its effective surface area. This increases the capacitive effect of the anode on a volumetric basis.

In various embodiments, an anode component may include several anode subcomponents which are electrically connected. In some of these embodiments, the anode subcomponents are physically interconnected and fixed together.

One or more interconnected electrodes comprising the anode are coupled to feedthrough assembly 103 for electrically connecting the anode to circuitry outside the case, in various embodiments. In some embodiments, multiple anode feedthrough assemblies are used. In some embodiments, the anode is coupled to conductive case 101. In anodic case embodiments, the cathode is coupled to a feedthrough assembly and isolated from case 101. Some anodic case embodiments can use terminal 103, which is attached to conductive case 101, to provide a connection between the anode and outside components such as circuitry. In other embodiments, both the anode and the cathode are connected to components through one or more feedthrough assemblies which are isolated from case 101.

Various capacitor stack configurations are within the scope of the present subject matter. Some embodiments include nine cathode subcomponent layers, twenty separator subcomponents, and twenty-eight anode subcomponents. One of these embodiments includes a combination of nine elements, with two additional separators and two additional anode layers. One way to form such a combination includes stacking eight elements including three anode layers and one element including two anode layers. The number of layers, and the number of elements, is selectable by a capacitor stack design and manufacturing process to achieve a desired capacitor power and thickness, in various embodiments.

Additional capacitor stack embodiments include eighteen cathodes, twenty-two separators, and fifty-eight anodes. Some of these embodiments include a combination of nineteen elements, with two additional separators and two additional anode layers. One way to form such a combination includes stacking eighteen elements including three anode layers and one element including two anode layers.

Additional embodiments, which do not feature these exact numbers of anodes, cathodes, and separators, fall within the scope of the present subject matter. In various additional embodiments, a separator disposed between electrode layers may include one, two, or more sheets of a separator material, such as kraft paper, in various embodiments. The number of layers, and the number of elements, are selectable by capacitor stack design and manufacturing processes to achieve a desired capacitor power and thickness, in various embodiments.

In various embodiments, the electrodes of the present subject matter are adapted to deliver improved energy levels. Various embodiments include a capacitor stack adapted to deliver between 7.0 Joules per cubic centimeter of capacitor stack volume and 8.5 Joules per cubic centimeter of capacitor stack volume. Some embodiments are adapted to deliver about 7.7 Joules per cubic centimeter of capacitor stack volume. In some embodiments, the anode has a capacitance of between approximately 0.70 and 0.85 microfarads per square centimeter when charged at approximately 550 volts. In various embodiments, these ranges are available at a voltage of between about 410 volts to about 610 volts.

In various embodiments, the stack is disposed in a case, and linked with other components, a state which affects some of these values. For example, in one packaged embodiment, including a case and terminals, the energy density available ranges from about 5.3 Joules per cubic centimeter of capacitor stack volume to about 6.3 Joules per cubic centimeter of capacitor stack volume. Some embodiments are adapted to deliver about 5.8 Joules per cubic centimeter of capacitor stack volume. In various embodiments, these ranges are available at a voltage of between about 410 volts to about 610 volts. The present subject matter additionally includes, but is not limited to, embodiments disclosed on or around pages 30-34 of related and commonly assigned Provisional U.S. Patent Application "Method and Apparatus for Single High Voltage Aluminum Capacitor Design," Ser. No. 60/588,905, filed on Jul. 16, 2004, incorporated herein by reference.

FIG. 2A shows an anode 202 according to one embodiment of the present subject matter. Anode 202 is shown before it is assembled into a capacitor stack, such as capacitor stack 102, illustrated in example FIG. 1A. Anode 202 includes a main body portion 204 having one or more connection members 206. In one embodiment, connection member 206 includes one or more distinct members attached to the anode by welding, staking, or by using another connection method and/or structure.

In various embodiments, connection member are defined by an excise performed on an anode. In some of these embodiments, a connection member protrudes from anode 202, defining a protruding connection member 206. It is understood that the shape of connection member may be achieved with additional shaping operations, such as casting or forging, without departing from the scope of the present subject matter. It is additionally understood that connection member maybe be comprised of a secondary structure which is attached to anode 202 using welding, in various embodiments. Additional embodiments employ other fixating methods to attach a secondary structure to a main anode body without departing from the scope of the present subject matter.

In various embodiments, anode 202 is processed to increase its surface area. In some embodiments, anode 202 is exposed to an etchant. In some of these embodiments, portions of anode 202 are etched, and portions of connection member 206 are not etched along with the rest of anode 202. In one of these embodiments, a resin mask is put on portions of connection member 206 to keep those masked portions from becoming etched during the etching process. As is discussed herein, this provides for unetched, non-porous sections which improve the weldability of anode edges with respect to each other. The present subject matter additionally includes, but is not limited to, embodiments disclosed on or around pages 102-106, 115-119 of related and commonly assigned Provisional U.S. Patent Application "Method and Apparatus for Single High Voltage Aluminum Capacitor Design," Ser. No. 60/588,905, filed on Jul. 16, 2004, incorporated herein by reference.

In one embodiment, the present subject matter includes capacitor stack having at least a first substantially planar electrode having a first connection member with an unetched portion. In the embodiment, the unetched portion at least partially defines a first aperture passing through the first connection member. The embodiment also includes at least a second substantially planar electrode having a second connection member in alignment with the first connection member defining a first connection surface. In the embodiment, the first and second connection members are connected, with the first aperture at least partially adjacent the second connection member, and where the unetched portion is produced by a process comprising: depositing a curable resin mask onto the electrode; curing the curable resin mask to the electrode; etching the electrode, the cured mask restricting the etch; removing the cured mask from the electrode; and anodizing the electrode. The present subject matter incorporates by reference, but is not limited to, additional connection structures and methods illustrated on or around pages 102-106, 115-119 of related and commonly assigned Provisional U.S. Patent Application "Method and Apparatus for Single High Voltage Aluminum Capacitor Design," Ser. No. 60/588,905, filed on Jul. 16, 2004, incorporated herein by reference.

Protruding connection member 206 includes a proximal section 208 and distal section 210. In the embodiment of FIG. 2A, connection member 206 is an L-shaped member. However, it can have other shapes. In one embodiment, a portion of a distal section 210 along its outer edge is unetched, as discussed above.

In one embodiment, proximal section 208 is connected to main body 204 and is defined in part by a pair of cut-out portions 212 and 214 located on opposing sides of proximal section 208. Distal section 210 is connected to a portion of proximal section 208, in various embodiments. In some embodiments, it is integral with proximal section 208. Distal section 210 is attached as a separate member, in some embodiments. In one embodiment, distal section 210 is defined in part by a cut-out portion 216 which is located between main body 204 and distal section 210, and a cut-out portion 218 which separates distal section 210 from main body 204. In this embodiment, connection member 206 is positioned within the overall D-shape of anode 202. In various embodiments, connection member 206 extends outside the D-shape of anode 202. The exact size of the connection member, and its placement with regards to the main body, is provided here for demonstration only, and it is understood that additionally embodiments, employing additional ratios of connection member size to main body size, and employing additional positioning schemes, are possible, without departing from the scope of the present subject matter.

Additionally pictured are apertures 252, 254. In various embodiments, apertures are circular. Apertures shaped otherwise are possible without departing from the scope of the present subject matter. In various embodiments, the apertures have an interior surface or face which is substantially orthogonal to the material through which the aperture pass. In some embodiments, apertures range from about 0.010 inches in diameter to about 0.025 inches in diameter. Some embodiments are larger than 0.025 inches. Various embodiments range from about 0.010 inches in diameter to about 0.012 inches in diameter. Aperture diameters are tied, in part, to the capability of manufacturing equipment, in various embodiments. Apertures, in various embodiments, are punched or drilled. In some embodiments, apertures are manufactured with processes producing a diameter within +/−0.001 inches of an intended diameter. Apertures, in various embodiments, are cylindrical or barrel shaped. In some additional embodiments, apertures are shaped like a partial cone.

Layers having apertures can be joined to other layers at the aperture in a number of ways. For example, in one embodiment the aperture, or rather the material defining the aperture, is welded to an adjacent layer. For example, in one embodiment welding is provided by a Lumonics JK702 Nd-YAG laser welder using settings of approximately 1.4 Joules at a frequency of 100 hertz. The laser power is approximately 110 Watts, the pulse height is approximately 22%, and the pulse width is approximately 1.4 msec. In various embodiments, the pulse width ranges from about 1.0 ms to about 2.5 ms and the energy level ranges from about 0.8 J to about 2.0 J. Some processes use a laser beam diameter which is from about 0.008 inches to about 0.011 inches. The laser beam is applied around the aperture and a layer adjacent the aperture. Additional embodiments are joined otherwise. Some embodiments are joined with a solid state welding process, such as a spot weld.

Some embodiments include apertures which have an occluding skin in an un-welded state, and which are apertures in a welded state. For example, in some embodiments, occluded apertures are formed with a punching or pressing process such that a skin remains and extends along a face of the layer with the skin occluding what would otherwise be an aperture. The skin, in various embodiments, melts during a welding operation, and defines an aperture.

Various processes join multiple layers using apertures. For example, in one embodiment, a stack of multiple anode layers are interconnected at apertures 252, 254. In additional embodiments anode layers and cathode layers are interconnected at apertures. In one embodiment, a number of anodes and cathodes are first interconnected, and then these interconnected layers are separated into electrically isolated groups. Various examples of separation, including cutting, are disclosed in this application. It should be noted that while two apertures are illustrated, one is possible. In additional embodiments, more than two are used.

In some embodiments, each anode in capacitor stack 102 includes a connection member such as connection member 206. But other configurations are possible. For example, in one embodiment, one anode layer in a stack of multiple abutting and interconnected anodes has a connection member 206, while the remaining anode layers in the stack do not have connection members. To illustrate, one embodiment includes a three-layer anode stack having one layer with a connection member 206 and two layers without connection members. The two layers without connection members are welded, staked, or otherwise interconnected to the layer having the connection member. Apertures can be used for this interconnection. In embodiments having apertures, welding occurs proximal the material defining the aperture and the adjacent layer. In various embodiments, a weld is drawn along this connection surface.

FIG. 2B shows a cathode 302 according to one embodiment of the present subject matter. Cathode 302 is shown before it is assembled into capacitor stack, such as the capacitor stack 102 shown in FIG. 1. Cathode 302 includes a main body portion 304 having one or more connection members 306. In various embodiments, connection member 306 is an integral portion of cathode 302, and is punched, laser-cut, or otherwise shaped from the cathode. In additional embodiments, connection member 306 includes one or more separate members attached to the cathode by welding, staking, or through other methods. The present subject matter additionally includes, but is not limited to, embodiments disclosed on or around pages 13-29 of related and commonly assigned Provisional U.S. Patent Application "Method and Apparatus for Single High Voltage Aluminum Capacitor Design," Ser. No. 60/588,905, filed on Jul. 16, 2004, incorporated herein by reference. In various embodiments, portions of connection member 306 are not coated in a titanium coating.

In one embodiment, connection member 306 includes a proximal section 308 and a distal section 310. In various embodiments, connection member 306 is an L-shaped member. However, additional embodiments have other shapes. In one embodiment, proximal section 308 is connected to main body 304 and is defined in part by a pair of cut-out portions 312 and 314 located on opposing sides of proximal section 308. Distal section 310 is connected to a portion of proximal section 308. In one embodiment, it is integrated with proximal section 308. In some embodiments, distal section 310 is attached as a separate member. In one embodiment, distal section 310 is defined in part by a cut-out portion 316 which is located between main body 304 and distal section 310, and a cut-out portion 318 which separates distal section 310 from main body 304. In this embodiment, connection member 306 is located within the general shape or outline of cathode 302. In various embodiments, connection member 306 extends further from the main body of cathode 302 or connection member 306 is more internal within the main body of cathode 302.

For instance, in various embodiments, connection members 206 and 306 may be in different positions along the edges or even within the main body portions of the capacitor layers 202 and 302. For instance, in some embodiments connection members 206 and 306 are located along edges 220 and 320 of the respective electrodes 202 and 302. In some embodiments, the portions are located along curved edges 222 and 322 of the respective electrodes 202 and 302. In various embodiments, the portions may be cut-out within main bodies 204 and 304.

In one embodiment, proximal section 308 of cathode 302 and proximal section 208 of anode 202 are located in different positions (relative to each other) on their respective electrodes, while distal sections 210 and 310 are generally commonly positioned. For instance, in one embodiment connection members 206 and 306 of the anode 202 and the cathode 302, respectively, are mirror images of each other. In some embodiments, connection members 206 and 306 have generally reverse images of each other. In some embodiments, connection members 206 and 306 can have different shapes or sizes relative to each other. For example, the distal portions on either the anode or the cathode can be longer or shorter than its opposing distal portion.

FIGS. 3A and 3B show an anode 202' and a cathode 302' according to one embodiment of the present subject matter. Anode 202' and cathode 302' are shown before being assembled into capacitor stack 102 as shown in FIG. 1. Anode 202' and cathode 302' are generally similar to anode 202 and cathode 302, respectively, except connection member 206' does not include a cut-out such as cut-out 212 of anode 202 and connection member 306' does not include a cut-out such as cut-out 318 of cathode 302. Various embodiments utilize other shapes and locations for connection members such as connection members 206, 206', 306, and 306'.

Figure 4:
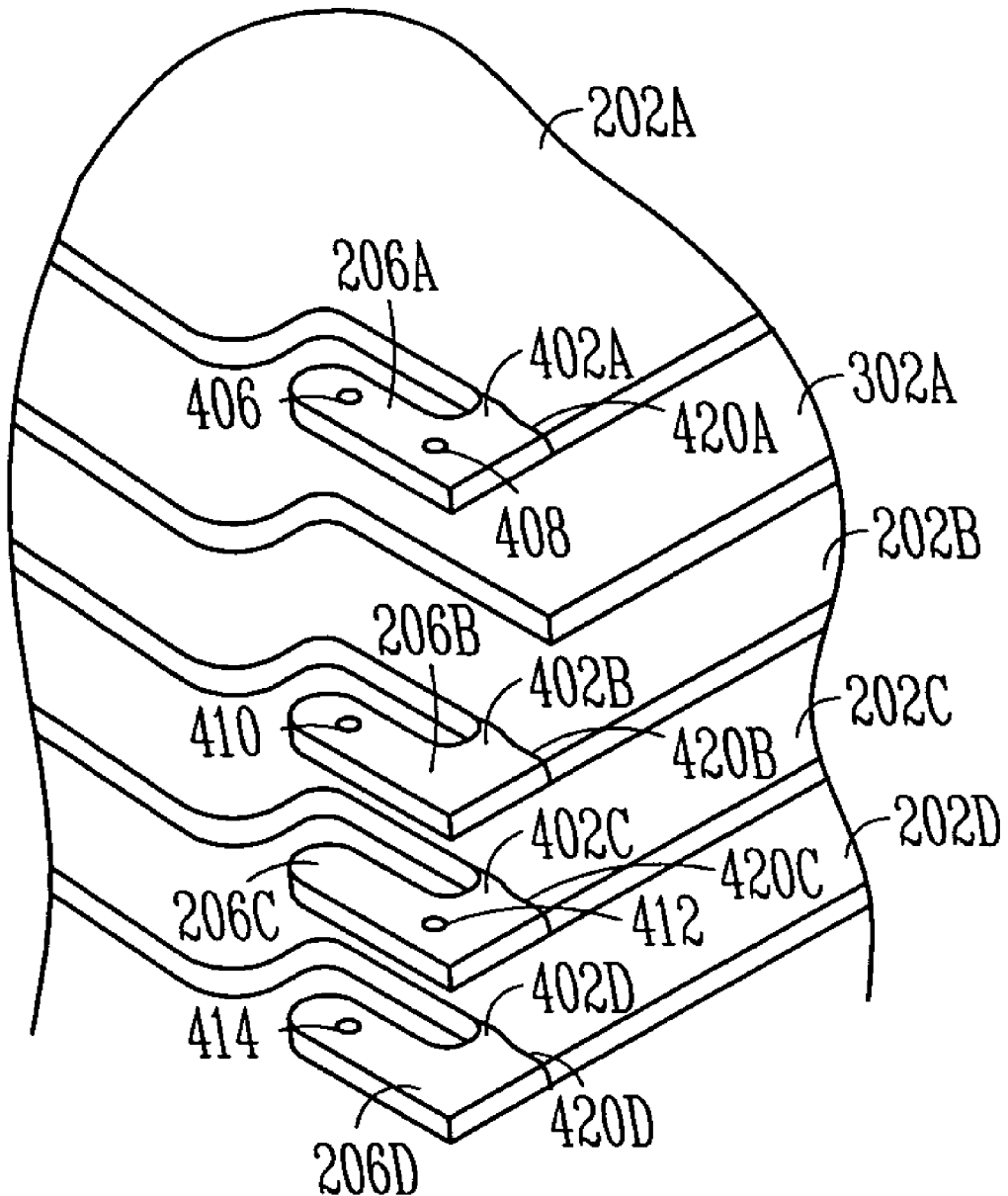
FIG. 4 is an exploded partial perspective view of capacitor stack layers, according to one embodiment of the present subject matter.

FIG. 4 is an exploded partial perspective view of capacitor stack layers, according to one embodiment of the present subject matter. The example illustrates one cathode layer 302A disposed between anode layers 202A, 202B. Additionally, the illustration depicts an anode group comprising anode layers 202B, 202C, and 202D. A capacitor stack of the present subject matter is not limited to this arrangement and configuration of anodes and cathodes; these illustrations are provided for discussion of one variant. For example, the exploded view excludes separator papers, which are disposed between anode layers and cathode layers in some embodiments.

Various capacitor embodiments include connection members 206A-D. In some of these embodiments, connection members are used to create an anode connection surface. In the example illustration, the connection members include an unetched portion 402A-D, and a gradient 420A-D between etched areas and unetched areas is visible. In various embodiments, creating an unetched portion 402A-D includes applying a mask to an anode layer during various production steps, or applying an etchant. The present subject matter additionally includes, but is not limited to, embodiments disclosed on or around pages 32-34 of related and commonly assigned Provisional U.S. Patent Application "Method and Apparatus for Single High Voltage Aluminum Capacitor Design," Ser. No. 60/588,905, filed on Jul. 16, 2004, incorporated herein by reference. Also, various embodiments include cathodes with titanium substantially absent, as is discussed above.

In varying embodiments apertures 406, 408, 410, 412, 414 are selectively distributed with respect to each other. In one embodiment, the apertures are circular. It is understood that other embodiments may have other shapes without departing from the scope of the present subject matter. In various embodiments, the apertures are positioned so as to not overlap while the layers are stacked in alignment. Using this method, a stack of electrode layers can be formed by moving a laser welding apparatus along a first axis and welding each layer to another layer placed on the stack. If the process employs only the first axis, cycle time required to weld the adjacent layers to one another can be reduced.

Welded layers, in various embodiments, create a physical and electrical connection. Selectively distributing apertures and connecting layers at the apertures provides a method for maintaining precision layer alignment. An added benefit is that the layers are electrically interconnected. Component size is reduced because of the high accuracy of welding operations, and the small size of apertures. Additionally, manufacturing efficiency benefits as the process does not require filler metal. Although filler metal is not required, the present subject matter is additionally compatible with processes using filler metal.

Figure 5:
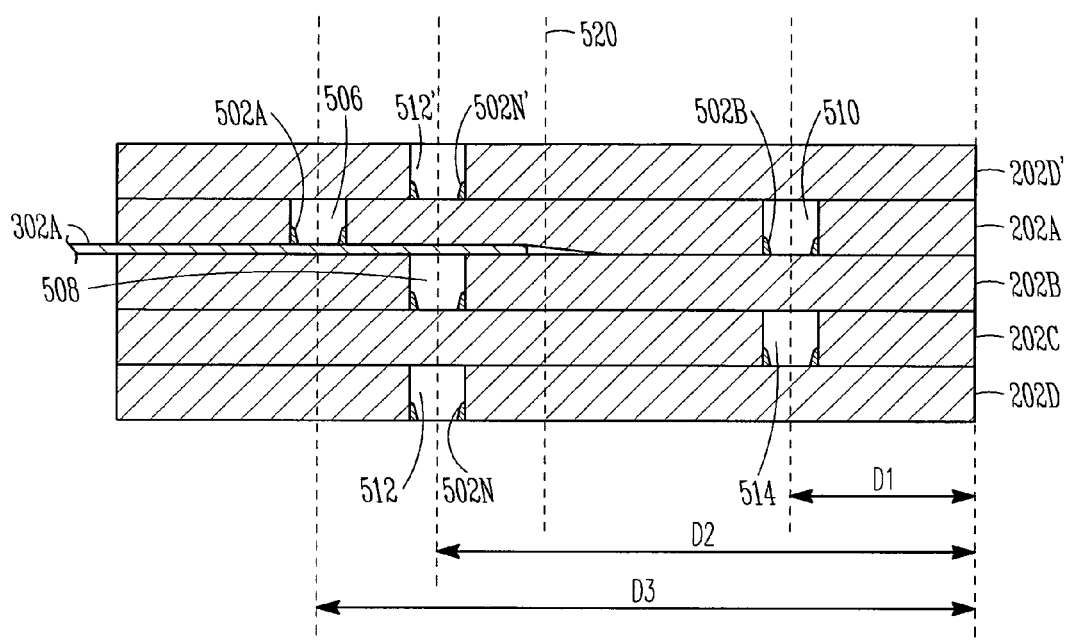
FIG. 5 is a partial cross section view of connection members in a stack, according to one embodiment of the present subject matter.

FIG. 5 is a partial cross section view of connection members in a stack, according to one embodiment of the present subject matter. The capacitor stack includes anode layers 202A-D, and cathode layer 302A. In various embodiments, the stack includes apertures 506, 508, 510, 512, 514, which, in various embodiments, are used for interconnecting additional components. In some embodiments, these capacitor stack layers are interconnected with laser welds 502A-N.

In various embodiments, two apertures can be located in a single layer, such as apertures 506 and 510. In additional embodiments, a layer has a single aperture, such as layer 202B. The arrangement of apertures is arbitrary, in that an aperture can be placed in any location and in any number within a layer. However, the selection is chosen, in various embodiments, to accomplish various objectives. One objective is to physically connect one layer to another in alignment. By welding the layers together, the layers are physically connected. By welding the layers as they are stacked, they maintain alignment during the stacking process. Dimensional accuracy in stacking is realized using this stacking method. Another objective is to electrically interconnect multiple layers. For example, in various embodiments, anode layers 202A-D can be electrically connected. Other objectives include enabling the creation of an anode connection surface by putting a series of edge faces into alignment for attachment of a terminal.

The following method is one way to create a capacitor stack. The method includes placing a first layer 202D on a working surface. The method then places a second layer 202C in alignment with the first layer 202D, and welds the second layer 202C to the first layer 202D along a connection surface. In various embodiments, a connection surface is defined by contacting portions in the vicinity of aperture 514 and first layer 202D. The weld can include filler material, or consume portions of one or both of the first layer 202D and the second layer 202C. This method of stacking and welding can be repeatedly used to form a capacitor of any desired thickness.

Interconnection options are increased by selecting various aperture configurations. This is illustrated, in various embodiments, by the distances D1, D2, and D3. By selecting D1 to be smaller than D2, the process allows that the second layer 202C can be welded to the first layer 202D along a connection surface at aperture 514. By selecting distance D2 to be less than distance D3, the process ensures that layer 202D' is stackable onto layer 202A in a manner which enables attachment. Other layers can be stacked onto the pictured stack and attached to the layers using apertures so long as the distances between the apertures of respective layers are selected such that material defining an aperture of one layer is adjacent material of another layer.

Additionally, various methods to create a capacitor stack include disposing a third layer 202B onto connected layers 202C and 202D. The third layer 202B, in various embodiments, is connected to the second layer 202C at the connection surface defined by the contact between aperture 508 and second layer 202C. A connection between layers 202B and 202C is created which physically constrains them and connects them electrically.

In various additional embodiments, a separator layer may be disposed between the third layer 202B and a cathode layer 302A. A separator layer may comprise one or more layers of kraft paper. The cathode layer 302A may be stacked onto an existing stack, such as stack 202B-D. A separator layer can then be disposed between cathode layer 302A and anode 202A.

It should be noted that in some embodiments, a separator layer does not extend to a connection surface. For example, an area for connection may extend away from a main capacitor stack portion. In these embodiments, connection members may be overlaid upon each other without separator. The connection members may all be interconnected, by a process such as edge welding. This includes connecting anodes to cathodes. The connection members are then separated with a cut, isolating the anodes from the cathodes, a process which, in some embodiments, leaves cathode portions which have been cut away from the main cathode connected to anode connection members. This is true also for embodiments in which portions of anode are cut away from the main anode and are interspersed among cathode connection members. In any of these embodiments, it is possible to create a connection surface without separator layers.

The illustration demonstrates weld 502A connecting cathode 302A to layer 202A. Additionally, weld 502B connects layer 202A to layer 202B. In various embodiments, one or more layers are deformed to achieve connection. For example, in one embodiment, layer 202A is deformed toward layer 202B to compensate for the presence of cathode layer 302A.

In some embodiments, the connection of layers 202A-D and 302 defines an element. In various embodiments, the element is electrically connected, and physically constrained in an alignment. In various embodiments, a cut may be made be made along line 520 to isolate anodes from cathodes.

Layer 202D' is included to demonstrate that additional capacitor subcomponents can be stacked onto the existing element. Additional components also benefit from apertures used for interconnection. For example, layer 202D' can be interconnected to an element including layers 202A-D at aperture 512' with weld 502N'.

Figure 6:
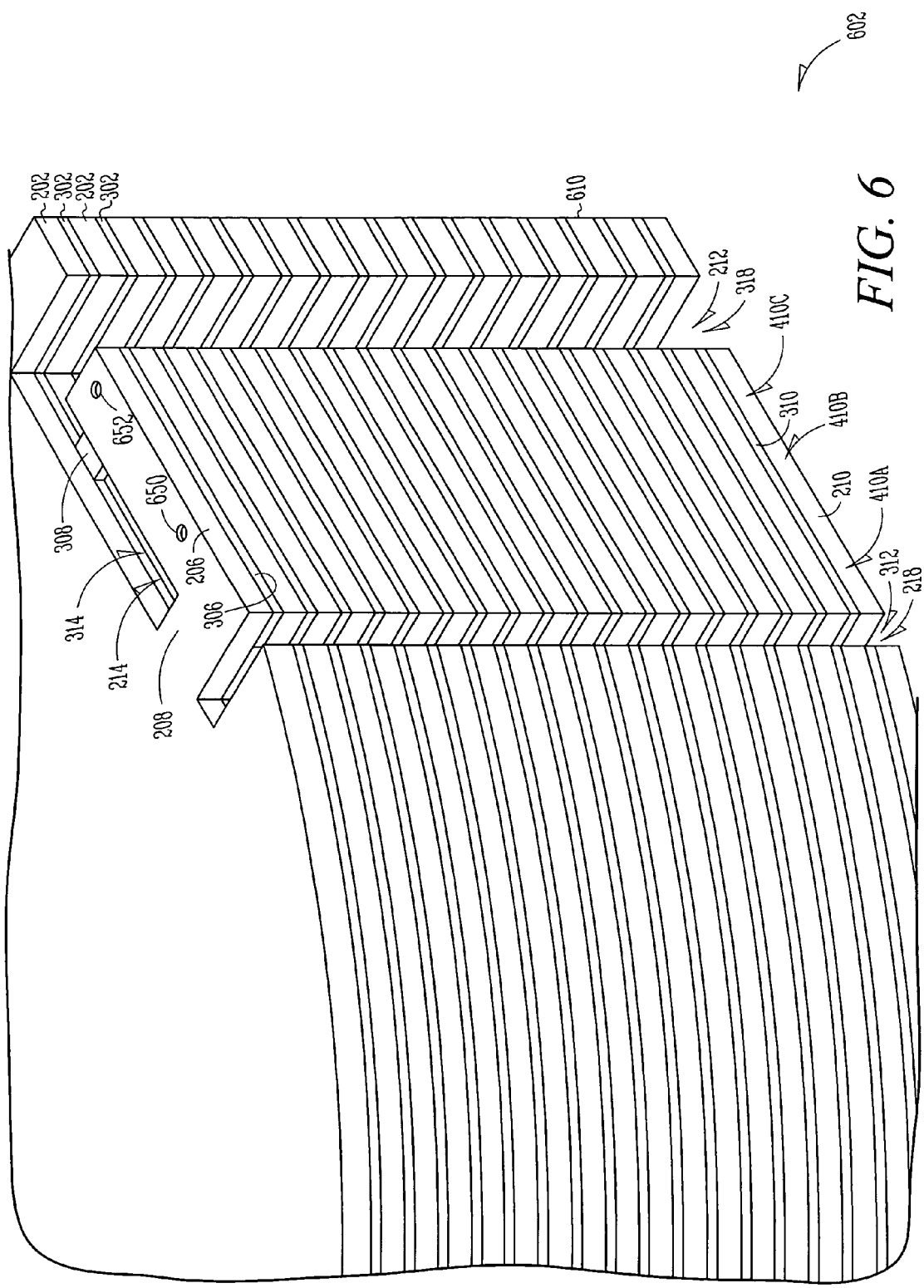
FIG. 6 is a partial perspective view of capacitor stack connection members, according to one embodiment of the present subject matter.

FIG. 6 shows a stack 700 of one or more alternating anodes 202 and cathodes 302. Connection members 206 and 306 are overlaying and underlying each other. As used herein, overlay and underlay refer to the position or location of portions of the layers which are commonly positioned from a top view. In various embodiments, connection members 206 and 306 have some commonly positioned portions relative to each other and some portions which are exclusively positioned relative to each other.

For instance, proximal sections 208 of anodes 202 are exclusively positioned or located. This means that at least a portion of proximal sections 208 do not overlay or underlay a portion of cathodes 302. Likewise, proximal sections 308 of cathodes 302 are exclusive portions and include at least a portion not overlaying or underlaying a portion of anode 202. Conversely, distal sections 210 and 310 are commonly positioned and each includes at least a portion overlaying or underlaying each another. Cut-out portions 214 and 314 are also commonly positioned. Cut-out 218 is commonly positioned with cut-out 312 while cut-out 212 is commonly positioned with cut-out 318.

When stacked as shown, the edges of distal sections 210 and 310 form a surface 610. In this embodiment, surface 610 can generally be described as having a first portion 410A which fronts the proximal sections 208 of anodes 202, a second portion 410B which fronts common cut-portions 214 and 314, and third portion 410C which fronts the proximal sections 308 of cathodes 302.

In this embodiment, distal sections 210 and 310 of anode connection member 206 and cathode connection member 306 are fully overlaying one another. Fully overlaying means that there are generally no gaps along surface 610 of stack 602 when the anodes and cathodes are stacked as in FIG. 6. The fully overlaid structure of stack 602 provides a complete surface 610 which provides for ease of edge-welding or otherwise connecting connection members 206 and 306 together. Additionally, various embodiments leave one or more gaps in surface 610 when the anodes and cathodes are stacked. For instance, in some embodiments, one or more of distal sections 210 or 310 may not reach all the way across front surface 610.

After being stacked, in various embodiments, at least portions of connection members 206 and 306 are connected to each other. For instance, in some embodiments, portions of distal sections 210 and 310 are connected to each other. In additional embodiments, distal sections 210 and 310 are edge-welded along surface 610. Additional embodiments include configuration where distal sections 210 and 310 are only connected along portion 410A and 410C of surface 610. Some embodiments also include configuration where distal sections 210 and 310 are soldered along surface 610. In various embodiments, portions of distal sections 310 and 210 are staked, swaged, laser-welded, or connected by an electrically conductive adhesive. Various embodiments include capacitor stacks where portions of proximal sections 208 are connected to each other and/or portions of proximal sections 308 are connected to each other.

In additional embodiments, apertures 650, 652 are used for interconnection anodes 202 and cathodes 302. One or more apertures may be used. The material defining the apertures in layer 202 is joined to layer 302 along a connection surface in the vicinity of the aperture. Various methods of joining are included in the present subject matter, including laser welding. It should be noted that various configurations of apertures are possible, in part, to ensure adjacent materials are positioned for connection. One embodiment staggers the apertures so that a process can include a repeating cycle of placing a layer and welding a layer, resulting in a stack which includes multiple interconnected anode layers and multiple interconnected cathode layers.

In various embodiments, after connection, portions of connection members 206 and 306 are removed or separated so that proximal sections 208 and 308 are electrically isolated from each other. As used herein, electrically isolated means that sections 208 and 308 are electrically insulated from each other at least up to a surge voltage of capacitor 100.

FIG. 7 shows stack 700 after portions of distal sections 210 and 310 (pictured in FIG. 6) have been removed from the stack, forming a cleave 702 between anode connection members 206, which together comprise anode connection surface 708, and cathode connection members 306, which together comprise cathode connection section or surface 710. Cleave 702 in the present embodiment electrically isolates surface 708 from surface 710. Cathodes in surface 710 are connected to anode portions with welds disposed along a connection surface inside apertures such as aperture 652. Additionally, anodes are connected to cathode portions in surface 708 along a connection surface inside apertures such as aperture 650.

Portions of cathodes remaining on the anode connection section or surface 708 have the titanium substantially absent from the aluminum substrate, enabling a weld which is substantially free of titanium. Welds which are substantially free of titanium develop improved oxides, which decreases leakage current in various examples.

Proximal sections 308 are still electrically coupled to each other as are proximal sections 208. In some embodiments, cleave 702 is a thin slice. In some embodiments, cleave 702 is as wide as cut-outs 214 and 314, as shown in FIG. 6. In some embodiments, an electrically insulative material is inserted in cleave 702. In various embodiments, cleave 702 is formed by laser cutting, punching, and/or tool or machine cutting.

One benefit of stacking anodes and cathodes as such is that the formation of anode connection surface 708 does not require excessive bending of anodes. For example, if portions of cathodes did not separate anodes, the anodes would have to be pressed together to deform into an anode connection surface. By allowing cathodes portions which are electrically isolated from the cathode of the capacitor to occupy the spaces between anode connection members, the need for these compressive forces is reduced, resulting in less bending stress on anodes, which can reduce instances of anode breakage.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and various embodiments, will be apparent to those of skill in the art upon reviewing the above description. The scope of the present subject matter should be determined with reference to the appended claims, along with the full scope of equivalents to which such claims are entitled.

What is claimed is:

1. A method of manufacturing a capacitor, comprising:
positioning a first substantially planar electrode including material of the first substantially planar electrode defining a first aperture into a capacitor stack in alignment with and on top of a second substantially planar electrode such that the first aperture is on top of a first non-aperture portion of the second substantially planar electrode and at least partially overlays the first non-aperture portion of the second substantially planar electrode, with the first non-aperture portion of the second substantially planar electrode extending across the first aperture to form a connection surface including the material of the first substantially planar electrode defining the first aperture and the first non-aperture portion of the second substantially planar electrode;
joining, along the connection surface, the first substantially planar electrode and the second substantially planar electrode, the joining proximal the material of the first substantially planar electrode defining the first aperture and the first non-aperture portion of the second substantially planar electrode;
disposing the capacitor stack into a capacitor case including terminals;
connecting the terminals to the capacitor stack;
filling the capacitor case with electrolyte; and
sealing the capacitor case with a seal which resists a flow of the electrolyte.

2. The method of claim 1, further comprising joining the first substantially planar electrode to the second substantially planar electrode by laser welding.

3. The method of claim 1, further comprising spraying an at least partially molten metal at the first substantially planar electrode proximal the first aperture.

4. The method of claim 1, further comprising joining a connection member including the first aperture to the first substantially planar electrode.

5. The method of claim 1, further comprising:
anodizing the second substantially planar electrode; and
insulating the first substantially planar electrode from the second substantially planar electrode by cutting only the second substantially planar electrode.

6. The method of claim 1, further comprising:
positioning a third substantially planar electrode including material defining a second aperture into the capacitor stack in alignment; and
joining the third substantially planar electrode to the second substantially planar electrode proximal the material defining the second aperture and a second non-aperture portion which at least partially overlays the second aperture of the second substantially planar electrode.

7. The method of claim 6, further comprising:
positioning a fourth substantially planar electrode into the capacitor stack in alignment; and
joining the fourth substantially planar electrode to the third substantially planar electrode proximal the material defining a third aperture in the third substantially planar electrode.

8. The method of claim 6, further comprising:
stacking the first substantially planar electrode and the second substantially planar electrode into a first element;
stacking the third substantially planar electrode, and a fourth electrode into a second element; and
stacking the first element and the second element in alignment.

9. The method of claim 6, further comprising at least partially etching the second substantially planar electrode by:
depositing a curable resin mask onto the second substantially planar electrode;
curing the curable resin mask to the second substantially planar electrode;
etching the second substantially planar electrode, the cured mask restricting the etch;
removing the cured resin from the second substantially planar electrode; and
anodizing the second substantially planar electrode.

10. The method of claim 9, further comprising partially etching the second substantially planar electrode such that first non-aperture portion is substantially unetched.

11. The method of claim 9, further comprising:
positioning a third substantially planar electrode including a second aperture into the capacitor stack in alignment; and
joining the third substantially planar electrode to the second substantially planar electrode along a second surface defined by the second aperture and a second non-aperture portion of the second substantially planar electrode.

12. The method of claim 11, further comprising:
stacking the first substantially planar electrode and the second substantially planar electrode into a first element;
stacking the third substantially planar electrode, and a fourth electrode into a second element; and
stacking the first element and the second element in alignment.

13. The method of claim 11, further comprising partially etching the second substantially planar electrode such that a second non-aperture portion is substantially unetched.

14. The method of claim 11, further comprising joining a connection member including the first aperture to the first substantially planar electrode at the first non-aperture portion.

15. The method of claim 1, wherein the first electrode is formed of aluminum.

16. The method of claim 1, further comprising:
disposing the capacitor case into a cardiac rhythm management device.

17. The method of claim 1, further comprising:
coupling a first connection member to a first substantially planar anode, the first connection member including material defining an aperture;
coupling a second connection member to a second substantially planar anode;
positioning the first substantially planar anode into a capacitor stack in alignment with the second substantially anode such that a non-aperture portion of the second connection member at least partially overlays the aperture of the first connection member;
joining the first connection member to the second connection member proximal the material defining the aperture;
stacking at least one cathode layer into the stack in alignment; and
disposing the stack in a capacitor case.

18. The method of claim 17, wherein joining the first connection member to the second connection member comprises welding.

19. The method of claim 18, wherein welding comprises laser welding.

20. The method of claim 17, wherein positioning the first substantially planar anode into a capacitor stack in alignment with the second substantially anode includes defining a connection surface along an edge of the first connection member and an edge of the second connection member, wherein welding including welding along the connection surface.

* * * * *